(12) United States Patent
Li et al.

(10) Patent No.: US 12,150,990 B2
(45) Date of Patent: Nov. 26, 2024

(54) PHARMACEUTICAL COMPOSITION OF HUMANIZED MONOCLONAL ANTI-PD-L1 ANTIBODY

(71) Applicants: NANJING SHUNXIN PHARMACEUTICAL CO., LTD., Jiangsu (CN); CHIA TAI TIANQING PHARMACEUTICAL GROUP CO., LTD, Jiangsu (CN)

(72) Inventors: Jianwen Li, Jiangsu (CN); Yanju Cheng, Jiangsu (CN); Yingchun Li, Jiangsu (CN); Wei Zhao, Jiangsu (CN); Xiquan Zhang, Jiangsu (CN)

(73) Assignees: NANJING SHUNXIN PHARMACEUTICAL CO., LTD., Jiangsu (CN); CHIA TAI TIANQING PHARMACEUTICAL GROUP CO., LTD, Jiangsu (CN)

(*) Notice: Subject to any disclaimer, the term of this patent is extended or adjusted under 35 U.S.C. 154(b) by 1261 days.

(21) Appl. No.: 16/756,409

(22) PCT Filed: Nov. 2, 2018

(86) PCT No.: PCT/CN2018/113579
§ 371 (c)(1),
(2) Date: Apr. 15, 2020

(87) PCT Pub. No.: WO2019/085982
PCT Pub. Date: May 9, 2019

(65) Prior Publication Data
US 2020/0237906 A1    Jul. 30, 2020

(30) Foreign Application Priority Data
Nov. 2, 2017    (CN) .................. 201711062923.X

(51) Int. Cl.
*A61K 39/395* (2006.01)
*A61K 47/02* (2006.01)
*A61K 47/10* (2017.01)
*A61K 47/14* (2017.01)
*A61K 47/26* (2006.01)
*C07K 16/28* (2006.01)
*A61K 39/00* (2006.01)

(52) U.S. Cl.
CPC .......... *A61K 39/3955* (2013.01); *A61K 47/02* (2013.01); *A61K 47/10* (2013.01); *A61K 47/14* (2013.01); *A61K 47/26* (2013.01); *C07K 16/2827* (2013.01); *A61K 2039/505* (2013.01); *A61K 2039/545* (2013.01); *C07K 2317/24* (2013.01)

(58) Field of Classification Search
None
See application file for complete search history.

(56) References Cited

U.S. PATENT DOCUMENTS

| | | | | |
|---|---|---|---|---|
| 8,217,149 | B2* | 7/2012 | Irving | A61K 39/39558 530/387.1 |
| 2006/0088523 | A1* | 4/2006 | Andya | A61K 47/26 424/133.1 |

FOREIGN PATENT DOCUMENTS

| | | |
|---|---|---|
| CN | 105793288 A | 7/2016 |
| CN | 106390115 A | 2/2017 |
| CN | 106432501 A | 2/2017 |
| CN | 107198773 A | 9/2017 |
| WO | 2013093809 A1 | 6/2013 |
| WO | 2015048520 A1 | 4/2015 |
| WO | 2015081158 A1 | 6/2015 |
| WO | 2016022630 A1 | 2/2016 |
| WO | 2017097407 A1 | 6/2017 |

OTHER PUBLICATIONS

Wang, Wei et al.; "Antibody Structure, Instability, and Formulation"; Journal of Pharmaceutical Sciences, American Chemical Society and American Pharmaceutical Assorciation, vol. 96, No. 1; Jan. 1, 2007; ISSN: 0022-3549; pp. 1-26.

* cited by examiner

*Primary Examiner* — Yunsoo Kim
(74) *Attorney, Agent, or Firm* — NKL Law; Allen Xue

(57) ABSTRACT

The invention is in the field of antibody formulations, and particularly relates to a pharmaceutical composition of a humanized monoclonal anti-PD-L1 antibody, wherein the pharmaceutical composition comprises 1-150 mg/ml of the humanized monoclonal anti-PD-L1 antibody, a buffer at 3-50 mM, 2-150 mg/ml of an isotonic adjuster/stabilizer and 0.01-0.8 mg/ml of a surfactant, and has a pH of about 4.5-6.8. The formulations prevent antibody aggregates therein from increasing, while enabling better maintenance of the biological binding activity of the antibody for a long time.

6 Claims, No Drawings
Specification includes a Sequence Listing.

PHARMACEUTICAL COMPOSITION OF HUMANIZED MONOCLONAL ANTI-PD-L1 ANTIBODY

INCORPORATION OF SEQUENCE LISTING

This application contains a sequence listing submitted in Computer Readable Form (CRF). The CFR file containing the sequence listing entitled "PA580-0001_ST25.txt", which was created on Apr. 14, 2020, and is 22,003 bytes in size. The information in the sequence listing is incorporated herein by reference in its entirety.

FIELD OF THE INVENTION

The invention is in the field of antibody formulations, and particularly relates to a pharmaceutical composition of a humanized monoclonal anti-PD-L1 antibody.

BACKGROUND ART

PD-L1 (Programmed Death-ligand 1), also known as CD247 and B7-H1, is one of the ligands for programmed death molecule 1 (Programmed death-1, PD-1). PD-L1 is highly expressed on the surface of various tumor cells, and its expression level is associated closely with malignancy of a tumor and poor prognosis. In the tumor microenvironment, upon binding to PD-1 or CD80 on the surface of T cells, PD-L1 on the surface of cancer cells, inhibits activation and proliferation of T cells, promotes depletion or unresponsiveness of effector T cells, induces apoptosis of T cells, and stimulates differentiation of helper T cells into regulatory T cells, thereby preventing T cells from killing tumor cells. Anti-PD-L1 antibodies can block the interaction of PD-L1 with PD-1 and CD80, so that the relevant negative regulatory signals can't be activated and transmitted, thereby avoiding inhibition of the activity of effector T cells in the tumor microenvironment. Thus, T cells can play a role in killing and suppressing tumor cells. Since anti-PD-1 antibodies are able to act directly on tumor tissues, the specificity and safety thereof are higher. At present, the drug products of monoclonal anti-PD-L1 antibodies prevailing internationally include atezolizumab from Roche and Durvalumab from AstraZeneca.

WO2016022630 discloses a new class of anti-PD-L1 antibodies, which have a high affinity for PD-L1, can inhibit significantly interaction of PD-L1 on the cell surface with PD-1, and promote significantly secretion of IL-2 and IFN-γ by T cells. Therefore, to improve its drugability, there is an urgent need to develop a formulation of anti-PD-L1 antibody for clinical therapy.

In the field of the antibody formulation, the formulation of proteins poses special problems because proteins are more complex than traditional organic and inorganic drugs. With the exception of poorly water-soluble compounds, physical instability is rarely encountered in pharmaceutical formulations of small molecules. However, a lot of structural changes with the exception of chemical modifications are prone to occur, due to the ability of proteins to integrate into highly ordered structures. Physical instability of a protein is more difficult to be controlled than chemical instability thereof. The exposed hydrophobic region will promote aggregation or self-association of the protein, which may result in physical instability and potential loss of the biological activity. To enable a protein to remain biologically active, a formulation must preserve intact the conformational integrity of a core sequence of the protein's amino acids, while at the same time protecting multiple functional groups of the protein from degradation and hindering protein aggregation.

The invention is effective in controlling the content of aggregates in the anti-PD-L1 antibody formulation and addressing the issues such as the increased content of aggregates and change in the antibody activity during the placement, thereby obtaining a highly stable formulation.

SUMMARY OF THE INVENTION

It is an aim of the present invention to at least provide a highly stable pharmaceutical composition, characterized in that: the pharmaceutical composition comprises an antibody, and at least one or more of a buffer, an isotonic adjuster, a stabilizer, and/or a surfactant. In particular, the pharmaceutical composition comprises 1-150 mg/ml of a humanized monoclonal anti-PD-L1 antibody (Mab), a buffer at 3-50 mM, 2-150 mg/ml of an isotonic adjuster/stabilizer, and 0.01-0.8 mg/ml of a surfactant, and has a pH of about 4.5-6.8. The formulation prevents the antibody aggregates therein from increasing, while enabling better maintenance of the biological binding activity of the antibody for a long time.

In some embodiments, the humanized monoclonal anti-PD-L1 antibody has a concentration by w/v of about 5-150 mg/ml; preferably about 10-60 mg/ml; more preferably about 10-30 mg/ml. In some particular embodiments, the humanized monoclonal anti-PD-L1 antibody has a mass concentration of about 10 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 110 mg/ml, or about 120 mg/ml, preferably about 10 mg/ml, about 20 mg/ml, about 30 mg/ml, about 40 mg/ml, about 50 mg/ml or about 60 mg/ml, more preferably about 10 mg/ml, about 20 mg/ml or about 30 mg/ml. In some embodiments, the humanized monoclonal anti-PD-L1 antibody has a mass concentration of about 10 mg/ml. In other embodiments, the humanized monoclonal anti-PD-L1 antibody has a mass concentration of about 30 mg/ml. In other embodiments, the humanized monoclonal anti-PD-L1 antibody has a mass concentration of about 60 mg/ml.

In some embodiments, the buffer is selected from the group consisting of a citrate buffer, an acetate buffer, a histidine salt buffer, or a phosphate buffer; preferably a citrate buffer or a histidine salt buffer; more preferably a histidine salt buffer. In some embodiments, the buffer has a concentration of about 4.5-50 mM, preferably about 5-25 mM, more preferably about 10-20 mM, and most preferably about 10-15 mM.

In some embodiments, the buffer is a histidine salt buffer. The buffer of the histidine salt has a concentration of about 5-30 mM, preferably about 10-25 mM, more preferably about 10-20 mM, and most preferably 10-15 mM. In some embodiments, the histidine salt buffer is at about 5 mM, about 10 mM, about 15 mM, about 20 mM, about 25 mM, or about 30 mM. In some embodiments, the histidine salt buffer is at about 10 mM. In other embodiments, the histidine salt buffer is at about 15 mM. In other embodiments, the histidine salt buffer is at about 20 mM. Wherein, the histidine salt buffer comprises histidine and hydrochloric acid.

In some embodiments, the buffer is an acetate buffer. The acetate buffer has a concentration of about 5-30 mM, preferably about 10-25 mM, more preferably about 10-20 mM, and most preferably about 10-15 mM. Wherein, the acetate buffer comprises acetate and acetic acid. The "an acetate" set forth in the present invention includes various pharmaceutically acceptable inorganic or organic salts of acetic acid or hydrates thereof, including but not limited to potassium acetate or hydrates thereof, sodium acetate or hydrates thereof, preferably the acetate being sodium acetate or sodium acetate trihydrate.

In some embodiments, the buffer is a citrate buffer. The citrate buffer has a concentration of about 3-30 mM, preferably about 4.5-30 mM, more preferably about 5-20 mM, and most preferably about 5-10 mM. In some embodiments, the citrate buffer is at about 5 mM, about 10 mM, about 15 mM, about 20 mM, or about 25 mM. In some embodiments, the citrate buffer is at about 5 mM. In other embodiments, the citrate buffer is at about 10 mM. In other embodiments, the citrate buffer is at about 15 mM. The "citric acid" set forth in the present invention includes citric acid itself and hydrates of citric acid, such as citric acid monohydrate; and the "citrate" includes various pharmaceutically acceptable inorganic or organic citrate salts or hydrates thereof, including but not limited to potassium citrate or hydrates thereof, sodium citrate or hydrates thereof; preferably the citrate being sodium citrate or dihydrate sodium citrate.

In some embodiments, the isotonic adjuster/stabilizer is selected from the group consisting of one or more of sodium chloride, mannitol, sucrose, trehalose, maltose, xylitol; preferably one or more of sodium chloride, mannitol and sucrose, and most preferably sucrose. In some embodiments, the content of the isotonic adjuster/stabilizer is about 4-150 mg/ml, preferably about 6-120 mg/ml, more preferably about 40-100 mg/ml, and most preferably about 60-80 mg/ml.

In some embodiments, the isotonic adjuster/stabilizer is sucrose at about 20-150 mg/ml, preferably of about 40-100 mg/ml, and more preferably of about 60-80 mg/ml on the basis of w/v. In some particular embodiments, the sucrose has a concentration of about 40 mg/ml, 50 mg/ml, 60 mg/ml, 70 mg/ml, 80 mg/ml, 90 mg/ml or 100 mg/ml. In some embodiments, the sucrose has a concentration of about 60 mg/ml. In some embodiments, the sucrose has a concentration of about 70 mg/ml. In some embodiments, the sucrose has a concentration of about 80 mg/ml. In some embodiments, the sucrose has a concentration of about 90 mg/ml.

In some particular embodiments, the isotonic adjuster/stabilizer is a sodium chloride solution at a concentration by w/v of about 5-20 mg/ml, preferably about 5-10 mg/ml, and more preferably about 6 mg/ml.

In some particular embodiments, the isotonic adjuster/stabilizer is mannitol at a concentration by w/v of about 10-40 mg/ml, preferably about 10-30 mg/ml of mannitol, and more preferably about of 20 mg/ml mannitol.

In some embodiments, the surfactant is selected from the group consisting of polysorbate-80, polysorbate-20, poloxamer 188; preferably polysorbate-80 or polysorbate-20; and more preferably polysorbate-80. In some embodiments, the surfactant has a concentration by w/v of about 0.05-0.6 mg/ml, preferably about 0.1-0.4 mg/ml, and more preferably about 0.2-0.3 mg/ml.

In some particular embodiments, the surfactant is polysorbate-80 or polysorbate-20 at about 0.01-0.8 mg/ml on the basis of w/v. In some embodiments, the surfactant is polysorbate-80 at about 0.05-0.6 mg/ml, preferably about 0.1-0.4 mg/ml, and more preferably about 0.2-0.3 mg/ml, and most preferably about 0.2 mg/ml. In some embodiments, the content of the polysorbate-80 in the pharmaceutical composition is about 0.1 mg/ml, 0.2 mg/ml, 0.3 mg/ml, 0.4 mg/ml, 0.5 mg/ml or 0.6 mg/ml; preferably about 0.2 mg/ml, 0.3 mg/ml, 0.4 mg/ml or 0.5 mg/ml; more preferably about 0.2 mg/ml, 0.3 mg/ml or 0.4 mg/ml; most preferably about 0.2 mg/ml. In some embodiments, the content of the polysorbate-80 in the pharmaceutical composition is about 0.1 mg/ml. In other embodiments, the content of the polysorbate-80 in the pharmaceutical composition is about 0.2 mg/ml. In some embodiments, the content of the polysorbate-80 in the pharmaceutical composition is about 0.3 mg/ml. In other embodiments, the content of the polysorbate-80 in the pharmaceutical composition is about 0.4 mg/ml. In some embodiments, the content of the polysorbate-80 in the pharmaceutical composition is about 0.5 mg/ml.

In some embodiments, the aqueous solution of the pharmaceutical composition has a pH value selected from 4.0-6.8; preferably 4.5-6.5; more preferably 5.5-6.0; most preferably 5.5. In some embodiments, the pH of the aqueous solution of the pharmaceutical composition is about 4.5, about 4.8, about 5.0, about 5.2, about 5.4, about 5.5, about 5.6, about 5.8, or about 6.0, preferably about 5.0, about 5.2, about 5.4, about 5.5, or about 5.6, and more preferably about 5.5. In some embodiments, the pH of the aqueous solution of the pharmaceutical composition is about 5.0. In some embodiments, the pH of the aqueous solution of the pharmaceutical composition is about 5.2. In some embodiments, the pH of the aqueous solution of the pharmaceutical composition is about 5.4. In some embodiments, the pH of the aqueous solution of the pharmaceutical composition is about 5.5. In some embodiments, the pH of the aqueous solution of the pharmaceutical composition is about 5.6. In some embodiments, the pH of the aqueous solution of the pharmaceutical composition is about 5.8. In some embodiments, the pH of the aqueous solution of the pharmaceutical composition is about 6.0.

Preferably, the humanized monoclonal anti-PD-L1 antibody provided by the present invention comprises the amino acid sequence as follows: a heavy chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) homology to the amino acid sequence shown in SEQ ID NO: 1 or SEQ ID NO: 4; a heavy chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) homology to the amino acid sequence shown in SEQ ID NO: 2 or SEQ ID NO: 5; a heavy chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) homology to the amino acid sequence shown in SEQ ID NO: 3 or SEQ ID NO: 6; a light chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) homology to the amino acid sequence shown in SEQ ID NO: 7 or SEQ ID NO: 10; a light chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) homology to the amino acid sequence shown in SEQ ID NO: 8 or SEQ ID NO: 11; a light chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) homology to the amino acid sequence shown in SEQ ID NO: 9 or SEQ ID NO: 12.

In a particular embodiment, the humanized monoclonal anti-PD-L1 antibody provided by the present invention comprises the amino acid sequence as follows: a heavy chain CDR1 region selected from SEQ ID NO: 1 or SEQ ID NO: 4; a heavy chain CDR2 region selected from SEQ ID NO: 2 or SEQ ID NO: 5; a heavy chain CDR3 region selected from SEQ ID NO: 3 or SEQ ID NO: 6; a light chain CDR1 region selected from SEQ ID NO: 7 or SEQ ID NO: 10; a light chain CDR2 region selected from SEQ ID NO: 8 or SEQ ID NO: 11; a light chain CDR3 region selected from SEQID NO: 9 or SEQ ID NO: 12.

Preferably, the humanized monoclonal anti-PD-L1 antibody provided by the present invention comprises the amino acid sequence as follows: a heavy chain variable region having at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) homology to the amino acid sequence shown in SEQ ID NO: 13 or SEQ ID NO: 14; a light chain variable region having at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%)) homology to the amino acid sequence shown in SEQ ID NO: 15 or SEQ ID NO: 16.

In a particular embodiment, the humanized monoclonal anti-PD-L1 antibody provided by the present invention comprises the amino acid sequence as follows: the heavy chain variable region as shown in SEQ ID NO: 13; the light chain variable region as shown in SEQ ID NO: 15.

In another particular embodiment, the humanized monoclonal anti-PD-L1 antibody provided by the present invention comprises the amino acid sequence as follows: the heavy chain variable region as shown in SEQ ID NO: 14; the light chain variable region as shown in SEQ ID NO: 16.

In one particular embodiment, the humanized monoclonal anti-PD-L1 antibody provided by the present invention comprises the heavy chain amino acid sequence as shown in SEQ ID NO: 17, and the light chain amino acid sequence as shown in SEQ ID NO: 18.

In another particular embodiment, the humanized monoclonal anti-PD-L1 antibody provided by the present invention comprises the heavy chain amino acid sequence as shown in SEQ ID NO: 19, and the light chain amino acid sequence as shown in SEQ ID NO: 20.

In another particular embodiment, the humanized monoclonal anti-PD-L1 antibody provided by the present invention comprises the heavy chain amino acid sequence as shown in SEQ ID NO: 21, and the light chain amino acid sequence as shown in SEQ ID NO: 18.

The humanized anti-PD-L1 antibody provided by the present invention may be an antibody of IgG1 or IgG4. Preferably, the humanized monoclonal anti-PD-L1 antibody is an antibody of IgG1, and more preferably a glycosylated antibody of IgG1.

In a particular embodiment of the present invention, the pharmaceutical composition comprises:
(a) the humanized monoclonal anti-PD-L1 antibody at a mass concentration of about 20 mg/mL,
(b) sucrose at a mass concentration of about 70 mg/mL,
(c) polysorbate-80 at a mass concentration of about 0.1 mg/ml,
(d) histidine at a molar concentration of about 20 mM, and
(e) optionally, hydrochloric acid in an appropriate amount, for adjusting the pH of the composition to about 5.0.

In yet another particular embodiment of the invention, the pharmaceutical composition comprises:
(a) the humanized monoclonal anti-PD-L1 antibody at a mass concentration of about 10 mg/mL,
(b) sodium chloride at a mass concentration of about 6 mg/mL,
(c) polysorbate-80 at a mass concentration of about 0.1 mg/ml, and
(d) a citrate at a molar concentration of about 5 mM, and the composition has a pH of about 6.0.

In another particular embodiment of the invention, the pharmaceutical composition comprises:
(a) the humanized monoclonal anti-PD-L1 antibody at a mass concentration of about 10 mg/mL,
(b) sucrose at a mass concentration of about 80 mg/mL,
(c) polysorbate-80 at a mass concentration of about 0.2 mg/ml,
(d) histidine at a molar concentration of about 10 mM, and
(e) optionally, hydrochloric acid in an appropriate amount, for adjusting the pH of the composition to about 5.5.

In a further particular embodiment of the invention, the pharmaceutical composition comprises:
(a) the humanized monoclonal anti-PD-L1 antibody at a mass concentration of about 50 mg/mL,
(b) sucrose at a mass concentration of about 80 mg/mL,
(c) polysorbate-80 at a mass concentration of about 0.3 mg/ml,
(d) histidine at a molar concentration of about 10 mM, and
(e) optionally, hydrochloric acid in an appropriate amount, for adjusting the pH of the composition to about 5.5.

In yet another more particular embodiment of the present invention, the pharmaceutical composition comprises:
(a) the humanized monoclonal anti-PD-L1 antibody at a mass concentration of about 100 mg/mL,
(b) sucrose at a mass concentration of about 80 mg/mL,
(c) polysorbate-80 at a mass concentration of about 0.5 mg/ml,
(d) histidine at a molar concentration of about 10 mM,
(e) optionally, hydrochloric acid in an appropriate amount, for adjusting the pH of the composition to about 5.5.

In yet another more particular embodiment of the present invention, the pharmaceutical composition comprises:
(a) the humanized monoclonal anti-PD-L1 antibody at a mass concentration of about 5 mg/mL,
(b) sodium chloride at a mass concentration of about 3 mg/mL,
(c) mannitol at a mass concentration of about 20 mg/ml,
(d) polysorbate-80 at a mass concentration of about 0.1 mg/ml, and
(e) an acetate at a molar concentration of about 10 mM, and the composition has a pH of about 4.5.

In a further particular embodiment of the invention, the pharmaceutical composition comprises:
(a) the humanized monoclonal anti-PD-L1 antibody at a mass concentration of about 30 mg/mL,
(b) sucrose at a mass concentration of about 80 mg/mL,
(c) polysorbate-80 at a mass concentration of about 0.2 mg/ml,
(d) histidine at a molar concentration of about 10 mM, and
(e) optionally, hydrochloric acid in an appropriate amount, for adjusting the pH of the composition to about 5.5.

In yet another particular embodiment of the invention, the pharmaceutical composition comprises:
(a) the humanized monoclonal anti-PD-L1 antibody at a mass concentration of about 60 mg/mL,
(b) sucrose at a mass concentration of about 80 mg/mL,
(c) polysorbate-80 at a mass concentration of about 0.2 mg/ml,
(d) histidine at a molar concentration of about 10 mM, and (e) optionally, hydrochloric acid in an appropriate amount, for adjusting the pH of the composition to about 5.5.

In a further particular embodiment of the invention, the pharmaceutical composition comprises:
(a) the humanized monoclonal anti-PD-L1 antibody at a mass concentration of about 10 mg/mL,
(b) sucrose at a mass concentration of about 70 mg/mL,
(c) polysorbate-80 at a mass concentration of about 0.4 mg/ml,
(d) histidine at a molar concentration of about 20 mM, and
(e) optionally, acetic acid in an appropriate amount, for adjusting the pH of the composition to about 6.5.

In a further particular embodiment of the invention, the pharmaceutical composition comprises:
(a) the humanized monoclonal anti-PD-L1 antibody at a mass concentration of about 10 mg/mL,
(b) sucrose at a mass concentration of about 80 mg/mL,
(c) polysorbate-80 at a mass concentration of about 0.2 mg/ml,
(d) histidine at a molar concentration of about 20 mM, and
(e) optionally, hydrochloric acid in an appropriate amount, for adjusting the pH of the composition to about 5.5.

In another particular embodiment of the invention, the pharmaceutical composition comprises:
(a) the humanized monoclonal anti-PD-L1 antibody at a mass concentration of about 10 mg/mL,
(b) sodium chloride at a mass concentration of about 6 mg/mL,
(c) polysorbate-80 at a mass concentration of about 0.2 mg/ml,
(d) a citrate at a molar concentration of about 10 mM, and and the composition has a pH of about 5.0.

In a further particular embodiment of the invention, the pharmaceutical composition comprises:
(a) the humanized monoclonal anti-PD-L1 antibody at a mass concentration of about 10 mg/mL,
(b) sodium chloride at a mass concentration of about 6 mg/mL,
(c) polysorbate-80 at a mass concentration of about 0.2 mg/ml, and
(d) a phosphate at a molar concentration of about 10 mM, and the composition has a pH of about 5.0.

In some embodiments, the pharmaceutical composition is a water-soluble injection which comprises, but is not limited to an unlyophilized water-soluble formulation or a water-soluble formulation reconstituted from the lyophilized powder. In other embodiments, the pharmaceutical composition is a lyophilized formulation. The lyophilized formulation refers to a formulation prepared by lyophilization of an aqueous solution. Lyophilization is a stabilization process in which a substance is first frozen, then the amount of the solvent is reduced by sublimation (the primary drying process), and then the amount of the solvent is further reduced by desorption (the secondary drying process), until the amount of the solvent reaches a value unsupportive of the biological activity or chemical reaction. The lyophilized formulation of the present invention can also be dried by other methods known in the art, such as spray drying and bubble drying.

The formulation provided by the present invention has aggregates of no more than 1.1%, preferably of no more than 0.9%, more preferably of no more than 0.5%, when stored at 2 to 8° C. or at 25° C. for at least 6 months.

In another aspect of the present invention, the present invention also provides a method for preparing the aforementioned pharmaceutical composition, comprising mixing the humanized monoclonal anti-PD-L1 antibody with other agents, such as one or more of the buffer, the isotonic adjuster/stabilizer and/or the surfactant.

In yet another aspect of the invention, the invention also provides a method for treating a tumorigenic condition in a subject, comprising administering to the subject the aforementioned pharmaceutical composition.

Unless specifically stated, "about" in the present invention means that a particular value given is varied within a range of ±5%, preferably ±2%, and more preferably ±1%. For example, a pH of about 5.5 refers to a pH of 5.5±5%, preferably 5.5±2%, and more preferably 5.5±1%.

The "aggregates" herein refers to the aggregates generated from aggregation of the humanized monoclonal anti-PD-L1 antibody due to the interaction of the amino acid residues on the peptide chains or hydrophobic or electrostatic interaction among molecules.

Herein, "a degradation product" refers to a product which is generated due to the humanized monoclonal anti-PD-L1 antibody undergoing reactions such as deamination or peptide chain breakage in an aqueous solution, and has a molecular weight lower than that of the humanized monoclonal anti-PD-L1 antibody.

The humanized monoclonal anti-PD-L1 antibody formulation of high-quality according to the present invention has high stability, which not only addresses the issue that the excessively high content of the aggregates in the product impacts the safety of the product, but also solves the issue that the increased content of the aggregates during the placement impacts stability of the formulation and maintenance of antibody activity.

DETAILED DESCRIPTION

In summary, the present invention relates to the following items:
1. A pharmaceutical composition of highly stability and activity, characterized in that the pharmaceutical composition comprises:
   i) a humanized monoclonal anti-PD-L1 antibody, and
   ii) one or more of a buffer, an isotonic adjuster and/or a surfactant; alternatively, the pharmaceutical composition comprises 1-150 mg/ml of the humanized monoclonal anti-PD-L1 antibody, the buffer at 3-50 mM, 2-150 mg/ml of the isotonic adjuster and 0.01-0.8 mg/ml of the surfactant, and has a pH of about 4.5-6.8.
2. The pharmaceutical composition of Item 1, wherein the humanized monoclonal anti-PD-L1 antibody has a concentration of about 5-150 mg/ml, preferably about 10-60 mg/ml, and more preferably about 10-30 mg/ml.
3. The pharmaceutical composition of Item 1, wherein the humanized monoclonal anti-PD-L1 antibody has a concentration of about 10 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 110 mg/ml or about 120 mg/ml, preferably about 10 mg/ml, about 20 mg/ml, about 30 mg/ml, about 40 mg/ml, about 50 mg/ml or about 60 mg/ml, more preferably about 10 mg/ml, about 20 mg/ml, or about 30 mg/ml.
4. The pharmaceutical composition of any of Items 1-3, wherein the buffer is selected from the group consisting of a citrate buffer, an acetate buffer or a histidine salt buffer, preferably a citrate buffer or a histidine salt buffer, and more preferably a histidine salt buffer.

5. The pharmaceutical composition of any of Items 1-3, wherein the buffer has a concentration of about 4.5-50 mM, preferably about 5-25 mM, more preferably about 10-20 mM, and most preferably about 10-15 mM.
6. The pharmaceutical composition of any of Items 1-5, wherein the buffer is a histidine salt buffer having a concentration of about 5-30 mM, preferably about 10-25 mM, more preferably about 10-20 mM, and most preferably 10-15 mM.
7. The pharmaceutical composition of any of Items 1-5, wherein the buffer is an acetate buffer having a concentration of about 5-30 mM, preferably about 10-25 mM, and more preferably about 10-20 mM, most preferably about 10-15 mM.
8. The pharmaceutical composition of any of Items 1-5, wherein the buffer is a citrate buffer having a concentration of about 3-30 mM, preferably about 4.5-30 mM, more preferably about 5-20 mM, and most preferably about 5-10 mM.
9. The pharmaceutical composition of any of Items 1-3, wherein the isotonic adjuster is selected from the group consisting of one or more of sodium chloride, mannitol, sucrose, trehalose, maltose, xylitol, preferably one or more of sodium chloride, mannitol and sucrose, and most preferably sucrose.
10. The pharmaceutical composition of any of Items 1-3, wherein the content of the isotonic adjuster is about 4-150 mg/ml, preferably about 6-120 mg/ml, more preferably about 40-100 mg/ml, and most preferably about 60-80 mg/ml.
11. The pharmaceutical composition of any of items 1-10, wherein the isotonic adjuster is sucrose at a concentration of about 20-150 mg/ml, preferably about 40-100 mg/ml sucrose, and more preferably about 60-80 mg/ml Sucrose.
12. The pharmaceutical composition of any of Items 1-10, wherein the isotonic adjuster is a sodium chloride solution at a concentration of about 5-20 mg/ml, preferably about 5-10 mg/ml, and more preferably about 6 mg/ml.
13. The pharmaceutical composition of any of Items 1-10, wherein the isotonic adjuster is mannitol at a concentration of about 10-40 mg/ml, preferably about 10-30 mg/ml of mannitol, and more preferably about of 20 mg/ml of mannitol.
14. The pharmaceutical composition of any of Items 1-3, wherein the surfactant is selected from the group consisting of polysorbate-80, polysorbate-20, poloxamer 188; preferably polysorbate-80 or polysorbate-20; and more preferably polysorbate-80.
15. The pharmaceutical composition of any of Items 1-3, wherein the buffer surfactant has a concentration of about 0.05-0.6 mg/ml, preferably about 0.1-0.4 mg/l, and more preferably about 0.2-0.3 mg/ml.
16. The pharmaceutical composition of any of Items 1-3, wherein the surfactant is polysorbate-80 at about 0.05-0.6 mg/ml (w/v), preferably about 0.1-0.4 mg/ml, and more preferably about 0.2-0.3 mg/ml, and most preferably about 0.2 mg/ml.
17. The pharmaceutical composition of Item 1, wherein the aqueous solution thereof has a pH value selected from 4.0-6.8; preferably 4.5-6.5; more preferably 5.5-6.0; most preferably 5.5.
18. The pharmaceutical composition of any of Items 1-17, wherein the pharmaceutical composition is an aqueous solution or a lyophilized powder.
19. The pharmaceutical composition of any of Items 1-18, wherein the humanized monoclonal anti-PD-L1 antibody comprises the amino acid sequence as follows: a heavy chain CDR1 region having at least 80% homology to the amino acid sequence shown in SEQ ID NO: 1 or SEQ ID NO: 4; a heavy chain CDR2 region having at least 80% homology to the amino acid sequence shown in SEQ ID NO: 2 or SEQ ID NO: 5; a heavy chain CDR3 region having at least 80% homology to the amino acid sequence shown in SEQ ID NO: 3 or SEQ ID NO: 6; a light chain CDR1 region having at least 80% homology to the amino acid sequence shown in SEQ ID NO: 7 or SEQ ID NO: 10; a light chain CDR2 region having at least 80% homology to the amino acid sequence shown in SEQ ID NO: 8 or SEQ ID NO: 11; a light chain CDR3 region having at least 80% homology to the amino acid sequence shown in SEQ ID NO: 9 or SEQ ID NO: 12.
20. The pharmaceutical composition of Item 19, wherein the humanized monoclonal anti-PD-L1 antibody comprises the amino acid sequence as follows: a heavy chain CDR1 region selected from SEQ ID NO: 1 or SEQ ID NO: 4; a heavy chain CDR2 region selected from SEQ ID NO: 2 or SEQ ID NO: 5; a heavy chain CDR3 region selected from SEQ ID NO: 3 or SEQ ID NO: 6; a light chain CDR1 region selected from SEQ ID NO: 7 or SEQ ID NO: 10; a light chain CDR2 region selected from SEQ ID NO: 8 or SEQ ID NO: 11; a light chain CDR3 region selected from SEQ ID NO: 9 or SEQ ID NO: 12.
21. The pharmaceutical composition of any of Items 1-18, wherein the humanized monoclonal anti-PD-L1 antibody comprises the amino acid sequence as follows: a heavy chain variable region having at least 80% homology to the amino acid sequence shown in SEQ ID NO: 13 or SEQ ID NO: 14; a light chain variable region having at least 80% homology to the amino acid sequence shown in SEQ ID NO: 15 or SEQ ID NO: 16.
22. The pharmaceutical composition of Item 21, wherein the humanized monoclonal anti-PD-L1 antibody comprises the amino acid sequence as follows: the heavy chain variable region as shown in SEQ ID NO: 13; the light chain variable region as shown in SEQ ID NO: 15.
23. The pharmaceutical composition of Item 21, wherein the humanized monoclonal anti-PD-L1 antibody comprises the amino acid sequence as follows: the heavy chain variable region as shown in SEQ ID NO: 14; light chain variable region as shown in SEQ ID NO: 16.
24. The pharmaceutical composition of any of Items 1-18, wherein the humanized monoclonal anti-PD-L1 antibody comprises the heavy chain amino acid sequence as shown in SEQ ID NO: 17, and the light chain amino acid sequence as shown in SEQ ID NO: 18.
25. The pharmaceutical composition of any of Items 1-18, wherein the humanized monoclonal anti-PD-L1 antibody comprises the heavy chain amino acid sequence as shown in SEQ ID NO: 19, and the light chain amino acid sequence as shown in SEQ ID NO: 20.
26. The pharmaceutical composition of any of Items 1-18, wherein the humanized monoclonal anti-PD-L1 antibody comprises the heavy chain amino acid sequence as shown in SEQ ID NO: 21, and the light chain amino acid sequence as shown in SEQ ID NO: 18.
27. The pharmaceutical composition of Item 1, the pharmaceutical composition comprising:
    (a) the humanized monoclonal anti-PD-L1 antibody at a mass concentration of about 20 mg/mL, (b) sucrose at a mass concentration of about 70 mg/mL,
(c) polysorbate-80 at a mass concentration of about 0.1 mg/ml,
(d) histidine at a molar concentration of about 20 mM, and
(e) optionally, hydrochloric acid in an appropriate amount, for adjusting the pH of the composition to about 5.0.

28. The pharmaceutical composition of Item 1, the pharmaceutical composition comprising:
(a) the humanized monoclonal anti-PD-L1 antibody at a mass concentration of about 10 mg/mL,
(b) sodium chloride at a mass concentration of about 6 mg/mL,
(c) polysorbate-80 at a mass concentration of about 0.1 mg/ml, and
(d) a citrate at a molar concentration of about 5 mM, and the composition has a pH of about 6.0.

29. The pharmaceutical composition of Item 1, the pharmaceutical composition comprising:
(a) the humanized monoclonal anti-PD-L1 antibody at a mass concentration of about 10 mg/mL,
(b) sucrose at a mass concentration of about 80 mg/mL,
(c) polysorbate-80 at a mass concentration of about 0.2 mg/ml,
(d) histidine at a molar concentration of about 10 mM, and
(e) optionally, hydrochloric acid in an appropriate amount, for adjusting the pH of the composition to about 5.5.

30. The pharmaceutical composition of Item 1, the pharmaceutical composition comprising:
(a) the humanized monoclonal anti-PD-L1 antibody at a mass concentration of about 50 mg/mL,
(b) sucrose at a mass concentration of about 80 mg/mL,
(c) polysorbate-80 at a mass concentration of about 0.3 mg/ml,
(d) histidine at a molar concentration of about 10 mM,
(e) optionally, hydrochloric acid in an appropriate amount, for adjusting the pH of the composition to about 5.5.

31. The pharmaceutical composition of Item 1, the pharmaceutical composition comprising:
(a) the humanized monoclonal anti-PD-L1 antibody with a mass and volume concentration of about 100 mg/mL,
(b) sucrose at a mass concentration of about 80 mg/mL,
(c) polysorbate-80 at a mass concentration of about 0.5 mg/ml,
(d) histidine at a molar concentration of about 10 mM, and
(e) optionally, hydrochloric acid in an appropriate amount, for adjusting the pH of the composition to about 5.5.

32. The pharmaceutical composition of Item 1, the pharmaceutical composition comprising:
(a) the humanized monoclonal anti-PD-L1 antibody at a mass concentration of about 5 mg/mL,
(b) sodium chloride at a mass concentration of about 3 mg/mL,
(c) mannitol at a mass concentration of about 20 mg/ml,
(d) polysorbate-80 at a mass concentration of about 0.1 mg/ml, and
(e) an acetate at a molar concentration of about 10 mM, and the composition has a pH of about 4.5.

33. The pharmaceutical composition of Item 1, the pharmaceutical composition comprising:
(a) the humanized monoclonal anti-PD-L1 antibody at a mass concentration of about 30 mg/mL,
(b) sucrose at a mass concentration of about 80 mg/mL,
(c) polysorbate-80 at a mass concentration of about 0.2 mg/ml,
(d) histidine at a molar concentration of about 10 mM, and
(e) optionally, hydrochloric acid in an appropriate amount, for adjusting the pH of the composition to about 5.5.

34. The pharmaceutical composition of Item 1, the pharmaceutical composition comprising:
(a) the humanized monoclonal anti-PD-L1 antibody at a mass concentration of about 60 mg/mL,
(b) sucrose at a mass concentration of about 80 mg/mL,
(c) polysorbate-80 at a mass concentration of about 0.2 mg/ml,
(d) histidine at a molar concentration of about 10 mM, and
(e) optionally, hydrochloric acid in an appropriate amount, for adjusting the pH of the composition to about 5.5.

35. The pharmaceutical composition of Item 1, the pharmaceutical composition comprising:
(a) the humanized monoclonal anti-PD-L1 antibody at a mass concentration of about 10 mg/mL,
(b) sucrose at a mass concentration of about 70 mg/mL,
(c) polysorbate-80 at a mass concentration of about 0.4 mg/ml,
(d) histidine at a molar concentration of about 20 mM, and
(e) optionally, acetic acid in an appropriate amount, for adjusting the pH of the composition to about 6.5.

36. The pharmaceutical composition of Item 1, the pharmaceutical composition comprising:
(a) the humanized monoclonal anti-PD-L1 antibody at a mass concentration of about 10 mg/mL,
(b) sucrose at a mass concentration of about 80 mg/mL,
(c) polysorbate-80 at a mass concentration of about 0.2 mg/ml,
(d) histidine at a molar concentration of about 20 mM, and
(e) optionally, hydrochloric acid in an appropriate amount, for adjusting the pH of the composition to about 5.5.

37. The pharmaceutical composition of Item 1, the pharmaceutical composition comprising:
(a) the humanized monoclonal anti-PD-L1 antibody at a mass concentration of about 10 mg/mL,
(b) sodium chloride at a mass concentration of about 6 mg/mL,
(c) polysorbate-80 at a mass concentration of about 0.2 mg/ml, and
(d) a citrate at a molar concentration of about 10 mM,
(e) and the composition has a pH of about 5.0.

38. The pharmaceutical composition of Item 1, the pharmaceutical composition comprising:
(a) the humanized monoclonal anti-PD-L1 antibody at a mass concentration of about 10 mg/mL,
(b) sodium chloride at a mass concentration of about 6 mg/mL,
(c) polysorbate-80 at a mass concentration of about 0.2 mg/ml, and
(d) a phosphate at a molar concentration of about 10 mM,
(e) and the composition has a pH of about 5.0.

39. A method for preparing the pharmaceutical composition of any of the preceding Items 1-38, comprising mixing the humanized monoclonal anti-PD-L1 antibody with one or more of the buffer, the isotonic adjuster and/or the surfactant.

40. A method for treating a tumorigenic condition in a subject, comprising administering to the subject a pharmaceutical composition of any of Items 1-38.

The present invention is further described below in conjunction with the particular embodiments. However, these embodiments in the present invention are only used to illustrate, but not to limit the scope of the present invention. Likewise, the invention is not limited to any of the specifically preferred embodiment described herein. A person of skill in the art is to understand that the equivalent replacements or the corresponding improvements made to the technical features of the present invention still fall within the scope of protection of the present invention. Unless otherwise specified, the reagents used in the following Examples are all commercially available, and the solutions can be prepared with the conventional technique in the art. The humanized monoclonal anti-PD-L1 antibody in the Examples was prepared according to the method described in WO2016022630. After affinity chromatography, the eluate containing the antibody was obtained according to a conventional method for antibody purification.

EXAMPLES 1-12

Preparation of the Humanized Monoclonal anti-PD-L1 Antibody 5G11 Injections

According to the preparation method for the formula of the formulation in Table 1: the buffer solution of interest was prepared and adjusted to the intended pH value with an acid-base adjuster. The eluate of the purified humanized monoclonal anti-PD-L1 antibody 5G11 was replaced with the prepared buffer solution of interest by ultrafiltration. After completion of the replacement, the corresponding isotonic adjuster/stabilizer and the surfactant in Table 1 were added, and the final concentration of the antibody was controlled to the intended target concentration. The resulting solution was filter-sterilized, aliquoted aseptically into in vials, stopped, capped, and passed by visual inspection.

The humanized monoclonal anti-PD-L1 antibody 5G11 comprises the heavy chain variable region sequence shown in SEQ ID NO: 13; and the light chain variable region sequence shown in SEQ ID NO: 15. The heavy chain amino acid sequence of the humanized monoclonal anti-PD-L1 antibody 5G11 in the Examples is shown in SEQ ID NO: 17, and the light chain amino acid sequence thereof is shown in SEQ ID NO: 18.

TABLE 1

Formulas of the formulations in the individual Examples

| | | Buffer (mmol/L) | | | Isotonic adjuster/ stabilizer (mg/mL) | | | | | |
|---|---|---|---|---|---|---|---|---|---|---|
| Example No. | Antibody 5G11 (mg/mL) | Histidine | Sodium acetate/ acetic acid | Sodium dihydrogen phosphate - disodium hydrogen phosphate | Sodium citrate/ citric acid | Sucrose | Sodium chloride | Mannitol | Polysorbate-80 (mg/mL) | pH adjuster | pH |
| 1 | 20 | 20 | / | / | / | 70 | / | / | 0.1 | hydrochloric acid | 5.0 |
| 2 | 10 | / | / | / | 5 | / | 6 | / | 0.1 | / | 6.0 |
| 3 | 10 | 10 | / | / | / | 80 | / | / | 0.2 | hydrochloric acid | 5.5 |
| 4 | 50 | 10 | / | / | / | 80 | / | / | 0.3 | hydrochloric acid | 5.5 |
| 5 | 100 | 10 | / | / | / | 80 | / | / | 0.5 | hydrochloric acid | 5.5 |
| 6 | 5 | / | 10 | / | / | / | 3 | 20 | 0.1 | / | 4.5 |
| 7 | 30 | 10 | / | / | / | 80 | / | / | 0.2 | hydrochloric acid | 5.5 |
| 8 | 60 | 10 | / | / | / | 80 | / | / | 0.2 | hydrochloric acid | 5.5 |
| 9 | 10 | 20 | / | / | / | 70 | / | / | 0.4 | Acetic acid | 6.5 |
| 10 | 10 | 20 | / | / | / | 80 | / | / | 0.2 | hydrochloric acid | 5.5 |
| 11 | 10 | / | / | / | 10 | / | 6 | / | 0.2 | / | 5.0 |
| 12 | 10 | / | / | 10 | / | / | 6 | / | 0.2 | / | 5.0 |

EXAMPLE 13

Quality Study on the Humanized Monoclonal anti-PD-L1 Antibody 5G11 Injections 12 batches of the humanized monoclonal anti-PD-L1 antibody 5G11 injections were prepared according to the methods of Examples 1-12. Each batch of the injections was subject to a comprehensive quality study, that is, assayed for protein aggregates and the fragments of the degradation product with molecular sieve chromatography (Size-Exclusion Chromatography, SEC) and capillary electrophoresis-sodium dodecyl sulfate (CE-SDS), assayed for charge heterogeneity with ion exchange chromatography (Cation Exchange chromatography, CEX), and assayed for the biological binding activity of the antibody with enzyme-linked immunosorbent assay (ELISA).

SEC assay: Performed on TSKgel molecular-sieve chromatographic column (manufacturer: TOSOH; model: TSKgel G3000 SWXL; size: 5 µm, 7.8×300), eluted with a buffer solution of $Na_2HPO_4$ containing NaCl at pH of 7.0±0.1 as the mobile phase, with the detection wavelength of 280 nm. The peak sequence under this chromatographic condition is sequentially as follows: the aggregate peak, the main peak, and the degradation product peak. The content percentages for the aggregate, the main peak and the degradation product were calculated by the area normalization method.

CEX assay: Performed on BioLCpropac™ chromatographic column (manufacturer: Thermo; model: ProPac WCX-10 BioLC Analytical; size: 4×250 mm), eluted with a buffer solution of $Na_2HPO_4$ containing NaCl at pH of 7.0±0.1 as the mobile phase, with the detection wavelength of 280 nm. The peak sequence under this chromatographic condition is sequentially as follows: the acidic zone, the main peak, and the basic zone. The content percentages for the acidic zone, the main peak, and the basic zone were calculated by the area normalization method.

ELISA assay: The PD-L1-mFc protein was coated on a microwell plate, washed and blocked. Then, the control article/test article was diluted to a specific concentration, incubated with the coated protein for binding, washed and incubated with a HRP-labeled goat anti-human IgG antibody. The microwell plate was washed to remove the unbound reactant, and the substrate (TMB) was added for colour development. The reaction was stopped with a stop solution. The absorbance value (OD) was measured at 450/650 nm on a microplate reader. The OD reading was positively correlated with the concentration of the control article/test article binding to the coated protein. A 4-parameter Logistic curve was fitted for concentration-absorbance of the solution. $EC_{50}$ values for the control article/test article were calculated in accordance to the fitted curve and compared each other, resulting the activity of the 5G11 antibody binding to PD-L1-mFc protein.

The result of 12 batches of the humanized monoclonal anti-PD-L1 antibody injections is shown in Table 2.

The results show that in the prescriptions of Examples 1 to 12 of the present invention, the content percentage for the SEC aggregate is 0.1% to 0.3%, the content percentage for the main peak is 99.6% to 99.9%, and the biological binding activities of the antibodies all remain above 80%, which meets the requirements. The results show that the humanized monoclonal anti-PD-L1 antibody 5G11 injections of the present invention have low content of aggregates, good quality, and stable activity.

EXAMPLE 14

Stability Study on the Humanized Monoclonal anti-PD-L1 Antibody 5G11 Injections at 2-8° C.

12 batches of the humanized monoclonal anti-PD-L1 antibody injection were prepared according to the methods of Examples 1-12. Each batch of the injections was placed in an environment at 2-8° C. and sampled for testing at Months 0, 1, 2, 3, and 6. Purity of the monoclonal antibody was determined by molecular sieve chromatography (SEC) and ion exchange chromatography (CEX), and the biological binding activity thereof by enzyme-linked immunosorbent assay (ELISA). Changes in the purities and activities of the monoclonal antibody injections during the placement at 2-8° C. was examined to evaluate the stability of the pharmaceutical composition of the present invention. The method for detecting the involved indicators is the same as in Example 13. The activity stability and the purities of the humanized monoclonal anti-PD-L1 antibody injections at 2-8° C. is found in Table 3.

TABLE 2

The result of the quality study on the humanized monoclonal anti-PD-L1 antibody 5G11 injections

| Example No. | SEC Purity (%) | | | CEX Purity (%) | | | CE-SDS purity (%) | | Activity (%) |
|---|---|---|---|---|---|---|---|---|---|
| | Aggregate | Main peak | Degradation product | Acidic zone | Main peak | Basic zone | Aglycosylated heavy chain | Low molecular weight impurities | |
| Example 1 | 0.1 | 99.9 | 0.0 | 30.5 | 63.3 | 6.2 | 0.4 | 1.9 | 92 |
| Example 2 | 0.1 | 99.9 | 0.0 | 30.6 | 63.1 | 6.2 | 0.4 | 1.7 | 96 |
| Example 3 | 0.1 | 99.9 | 0.0 | 30.9 | 63.1 | 6.0 | 0.4 | 1.8 | 101 |
| Example 4 | 0.1 | 99.9 | 0.0 | 30.6 | 63.2 | 6.2 | 0.4 | 1.9 | 93 |
| Example 5 | 0.3 | 99.7 | 0.0 | 30.5 | 63.3 | 6.2 | 0.4 | 2.0 | 95 |
| Example 6 | 0.1 | 99.9 | 0.0 | 30.4 | 63.4 | 6.2 | 0.4 | 1.9 | 91 |
| Example 7 | 0.2 | 99.7 | 0.0 | 27.3 | 67.4 | 5.3 | 0.4 | 3.4 | 103 |
| Example 8 | 0.3 | 99.6 | 0.0 | 26.9 | 65.9 | 7.2 | 0.3 | 3.3 | 81 |
| Example 9 | 0.1 | 99.8 | 0.1 | 46.5 | 50.7 | 2.8 | 0.3 | 1.9 | 93 |
| Example 10 | 0.2 | 99.8 | 0.0 | 28.6 | 62.2 | 9.2 | 0.3 | 2.8 | 90 |
| Example 11 | 0.1 | 99.8 | 0.1 | 30.3 | 63.3 | 6.4 | 4.4 | 0.1 | 103 |
| Example 12 | 0.1 | 99.9 | 0.1 | 30.2 | 63.6 | 6.2 | 2.3 | 0.1 | 96 |

TABLE 3

Result of placement stability examination of the humanized monoclonal anti-PD-L1 antibody 5G11 injections at 2-8° C.

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| Example 1 | Day 0 | 0.1 | 99.9 | 0.0 | 30.5 | 63.3 | 6.2 | 92 |
| | Month 1 | 0.1 | 99.8 | 0.0 | 30.6 | 62.8 | 6.7 | 86 |
| | Month 2 | 0.1 | 99.8 | 0.0 | 30.7 | 62.5 | 6.8 | 101 |
| | Month 3 | 0.1 | 99.8 | 0.0 | 31.2 | 62.0 | 6.8 | 94 |
| | Month 6 | 0.2 | 99.8 | 0.1 | 31.4 | 61.7 | 6.9 | 94 |
| Example 2 | Day 0 | 0.1 | 99.9 | 0.0 | 30.6 | 63.1 | 6.2 | 96 |
| | Month 1 | 0.2 | 99.8 | 0.1 | 31.2 | 62.5 | 6.3 | 102 |
| | Month 2 | 0.2 | 99.8 | 0.1 | 30.7 | 62.7 | 6.6 | 85 |
| | Month 3 | 0.2 | 99.7 | 0.1 | 31.0 | 61.1 | 6.6 | 95 |
| | Month 6 | 0.2 | 99.7 | 0.1 | 31.3 | 58.5 | 7.1 | 101 |
| Example 3 | Day 0 | 0.1 | 99.9 | 0.0 | 30.9 | 63.1 | 6.0 | 100 |
| | Month 1 | 0.1 | 99.8 | 0.0 | 31.1 | 63.0 | 5.9 | 85 |
| | Month 2 | 0.2 | 99.8 | 0.0 | 30.6 | 62.4 | 6.2 | 94 |
| | Month 3 | 0.2 | 99.8 | 0.1 | 31.0 | 62.0 | 6.3 | 93 |
| | Month 6 | 0.2 | 99.8 | 0.1 | 31.5 | 59.2 | 6.6 | 102 |
| Example 4 | Day 0 | 0.1 | 99.9 | 0.0 | 30.6 | 63.2 | 6.2 | 93 |
| | Month 1 | 0.1 | 99.8 | 0.0 | 31.0 | 62.5 | 6.4 | 105 |
| | Month 2 | 0.2 | 99.8 | 0.0 | 30.8 | 62.3 | 6.5 | 100 |
| | Month 3 | 0.1 | 99.8 | 0.0 | 31.1 | 60.8 | 6.7 | 91 |
| | Month 6 | 0.2 | 99.8 | 0.1 | 31.5 | 59.0 | 7.2 | 85 |
| Example 5 | Day 0 | 0.3 | 99.7 | 0.0 | 30.5 | 63.3 | 6.2 | 105 |
| | Month 1 | 0.3 | 99.7 | 0.0 | 30.8 | 62.1 | 6.7 | 86 |
| | Month 2 | 0.3 | 99.7 | 0.0 | 31.2 | 61.5 | 6.7 | 93 |
| | Month 3 | 0.4 | 99.6 | 0.0 | 31.0 | 60.7 | 6.9 | 92 |
| | Month 6 | 0.5 | 99.4 | 0.1 | 31.5 | 59.3 | 7.1 | 98 |
| Example 6 | Day 0 | 0.1 | 99.9 | 0.0 | 30.4 | 63.4 | 6.2 | 91 |
| | Month 1 | 0.1 | 99.8 | 0.0 | 30.7 | 63.0 | 5.9 | 82 |
| | Month 2 | 0.2 | 99.8 | 0.0 | 30.6 | 62.2 | 6.2 | 93 |
| | Month 3 | 0.2 | 99.8 | 0.1 | 30.8 | 61.8 | 6.7 | 101 |
| | Month 6 | 0.2 | 99.7 | 0.1 | 31.1 | 59.3 | 7.1 | 96 |
| Example 7 | Day 0 | 0.2 | 99.7 | 0.0 | 27.3 | 67.4 | 5.3 | 103 |
| | Month 1 | 0.3 | 99.7 | 0.0 | 28.4 | 65.2 | 6.3 | 97 |
| | Month 2 | 0.2 | 99.7 | 0.1 | 30.4 | 62.8 | 6.7 | 97 |
| | Month 3 | 0.2 | 99.7 | 0.1 | 27.7 | 64.0 | 8.3 | 80 |
| | Month 6 | 0.3 | 99.7 | 0.0 | 28.6 | 62.4 | 9.1 | 82 |
| Example 8 | Day 0 | 0.3 | 99.6 | 0.0 | 26.9 | 65.9 | 7.2 | 81 |
| | Month 1 | 0.3 | 99.6 | 0.1 | 25.2 | 67.5 | 7.3 | 92 |
| | Month 2 | 0.3 | 99.6 | 0.0 | 25.6 | 68.5 | 5.8 | 103 |
| | Month 3 | 0.3 | 99.6 | 0.2 | 27.3 | 67.6 | 5.2 | 95 |
| | Month 6 | 0.4 | 99.4 | 0.2 | 29.2 | 65.6 | 5.2 | 100 |
| Example 9 | Day 0 | 0.1 | 99.8 | 0.1 | 46.5 | 50.7 | 2.8 | 93 |
| | Month 1 | 0.8 | 99.1 | 0.1 | 46.7 | 50.3 | 3.0 | 98 |
| | Month 2 | 0.8 | 99.0 | 0.1 | 45.7 | 48.7 | 5.5 | 91 |
| | Month 3 | 0.9 | 99.0 | 0.1 | 49.4 | 47.7 | 2.9 | 90 |
| | Month 6 | 1.0 | 98.9 | 0.1 | 50.1 | 44.3 | 5.6 | 86 |
| Example 10 | Day 0 | 0.2 | 99.8 | 0.0 | 28.6 | 62.2 | 9.2 | 90 |
| | Month 1 | 0.2 | 99.7 | 0.1 | 28.8 | 62.3 | 8.9 | 90 |
| | Month 2 | 0.2 | 99.7 | 0.1 | 28.6 | 63.4 | 8.0 | 90 |
| | Month 3 | 0.2 | 99.7 | 0.1 | 28.9 | 62.9 | 8.2 | 84 |
| | Month 6 | 0.2 | 99.7 | 0.0 | 29.0 | 62.3 | 8.8 | 102 |
| Example 11 | Day 0 | 0.1 | 99.8 | 0.1 | 30.3 | 63.4 | 6.4 | 103 |
| | Month 1 | 0.1 | 99.8 | 0.1 | 31.1 | 63.1 | 5.8 | 91 |
| | Month 2 | 0.2 | 99.8 | 0.1 | 30.8 | 63.3 | 5.9 | NA |
| | Month 3 | 0.2 | 99.6 | 0.3 | 31.3 | 61.9 | 6.8 | 114 |
| | Month 6 | 0.3 | 99.4 | 0.3 | 33.1 | 59.4 | 7.5 | 95 |
| Example 12 | Day 0 | 0.1 | 99.9 | 0.1 | 30.2 | 63.6 | 6.2 | 96 |
| | Month 1 | 0.1 | 99.7 | 0.1 | 31.3 | 63.7 | 5.0 | 107 |
| | Month 2 | 0.2 | 99.8 | 0.1 | 30.9 | 63.4 | 5.7 | 98 |
| | Month 3 | 0.2 | 99.8 | 0.1 | 31.5 | 62.5 | 6.0 | 108 |
| | Month 6 | 0.3 | 99.5 | 0.2 | 33.1 | 60.6 | 6.3 | 101 |

The results show that after the samples of the formulation prescriptions of Examples 1 to 8 and Examples 10 to 12 of the present invention have been placed at 2 to 8° C. for 6 months, the content percentage of the aggregate, which is 0.2% to 0.5%, is increased only by 0.1% to 0.2%; that of the main peak decreased only by 0.1% to 0.4%; that of the acidic zone increased by 0.4% to 2.9%; that of the basic zone changes slightly. All of the changes in the percentage were small. The results show that after the humanized monoclonal anti-PD-L1 antibody 5G11 injections of the present invention have been placed at 2 to 8° C. for 6 months, the content percentages for the aggregate and the degradation product have no substantial change, and the changes in the content percentages for the acidic and basic zones are controlled within a certain range, and the biological binding activity remains above 80%, indicating that the above-mentioned formulation prescriptions are highly stable.

EXAMPLE 15

Stability Study on the Humanized Monoclonal anti-PD-L1 Antibody 5G11 Injections at 25° C.

12 batches of the humanized monoclonal anti-PD-L1 antibody injection were prepared according to the methods of Examples 1-12. Each batch of the injections was placed in an environment at 25° C. and sampled for testing at Months 0, 1, 2, 3, and 6. Purity of the monoclonal antibody was determined by molecular sieve chromatography (SEC) and ion exchange chromatography (CEX), and the biological binding activity thereof by enzyme-linked immunosorbent assay (ELISA). Changes in the purities and activities of the humanized monoclonal anti-PD-L1 antibody injections during the placement at 25° C. was examined to evaluate the stability of the pharmaceutical composition of the present invention. The method for detecting the involved indicators is the same as in Example 13. The stability in the purities and the activities of the humanized monoclonal anti-PD-L1 antibody 5G11 injections at 25° C. is found in Table 4.

TABLE 4

Placement stability of the humanized monoclonal anti-PD-L1 antibody 5G11 injections at 25° C.

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| Example 1 | Day 0 | 0.1 | 99.9 | 0.0 | 30.5 | 63.3 | 6.2 | 92 |
| | Month 1 | 0.1 | 99.8 | 0.1 | 31.7 | 61.4 | 7.0 | 90 |
| | Month 2 | 0.2 | 99.7 | 0.1 | 32.7 | 59.6 | 7.7 | 100 |
| | Month 3 | 0.2 | 99.7 | 0.1 | 34.1 | 57.5 | 8.4 | 94 |
| | Month 6 | 0.3 | 99.5 | 0.2 | 37.6 | 53.0 | 9.5 | 93 |
| Example 2 | Day 0 | 0.1 | 99.9 | 0.0 | 30.6 | 63.1 | 6.2 | 96 |
| | Month 1 | 0.1 | 99.8 | 0.1 | 31.6 | 61.5 | 6.9 | 95 |
| | Month 2 | 0.2 | 99.8 | 0.1 | 32.8 | 59.5 | 7.7 | 86 |
| | Month 3 | 0.2 | 99.7 | 0.1 | 34.2 | 57.6 | 8.1 | 100 |
| | Month 6 | 0.3 | 99.5 | 0.2 | 37.8 | 53.1 | 9.2 | 92 |
| Example 3 | Day 0 | 0.1 | 99.9 | 0.0 | 30.9 | 63.1 | 6.0 | 100 |
| | Month 1 | 0.1 | 99.8 | 0.1 | 31.9 | 61.6 | 6.5 | 81 |
| | Month 2 | 0.2 | 99.8 | 0.1 | 32.9 | 60.0 | 7.1 | 88 |
| | Month 3 | 0.2 | 99.7 | 0.1 | 33.9 | 58.6 | 7.5 | 93 |
| | Month 6 | 0.3 | 99.5 | 0.2 | 37.0 | 54.4 | 8.6 | 105 |
| Example 4 | Day 0 | 0.1 | 99.9 | 0.0 | 30.6 | 63.2 | 6.2 | 93 |
| | Month 1 | 0.2 | 99.8 | 0.1 | 31.7 | 61.3 | 7.0 | 105 |
| | Month 2 | 0.2 | 99.7 | 0.1 | 32.8 | 59.5 | 7.7 | 100 |
| | Month 3 | 0.2 | 99.7 | 0.1 | 34.0 | 57.9 | 8.1 | 91 |
| | Month 6 | 0.3 | 99.4 | 0.3 | 38.1 | 52.5 | 9.4 | 85 |
| Example 5 | Day 0 | 0.3 | 99.7 | 0.0 | 30.5 | 63.3 | 6.2 | 105 |
| | Month 1 | 0.3 | 99.6 | 0.1 | 31.9 | 61.1 | 6.9 | 93 |
| | Month 2 | 0.4 | 99.5 | 0.1 | 33.1 | 59.4 | 7.5 | 86 |
| | Month 3 | 0.5 | 99.3 | 0.2 | 34.2 | 57.8 | 8.1 | 93 |
| | Month 6 | 0.9 | 98.8 | 0.3 | 47.2 | 44.4 | 8.4 | 101 |
| Example 6 | Day 0 | 0.1 | 99.9 | 0.0 | 30.4 | 63.4 | 6.2 | 91 |
| | Month 1 | 0.1 | 99.8 | 0.1 | 31.5 | 61.7 | 6.8 | 84 |
| | Month 2 | 0.2 | 99.8 | 0.1 | 32.6 | 60.2 | 7.2 | 95 |
| | Month 3 | 0.2 | 99.7 | 0.1 | 33.8 | 58.5 | 7.7 | 101 |
| | Month 6 | 0.3 | 99.5 | 0.2 | 37.2 | 53.7 | 9.1 | 94 |
| Example 7 | Day 0 | 0.2 | 99.7 | 0.0 | 27.3 | 67.4 | 5.3 | 103 |
| | Month 1 | 0.3 | 99.6 | 0.1 | 29.0 | 65.8 | 5.2 | 103 |
| | Month 2 | 0.3 | 99.5 | 0.2 | 31.5 | 61.8 | 6.7 | 95 |
| | Month 3 | 0.3 | 99.5 | 0.3 | 32.3 | 59.3 | 8.5 | 89 |
| | Month 6 | 0.7 | 98.9 | 0.4 | 43.6 | 47.5 | 8.9 | 106 |
| Example 8 | Day 0 | 0.3 | 99.6 | 0 | 26.9 | 65.9 | 7.2 | 81 |
| | Month 1 | 0.3 | 99.6 | 0.1 | 28.5 | 65.5 | 6.0 | 88 |
| | Month 2 | 0.4 | 99.5 | 0.2 | 29.4 | 64.9 | 5.8 | 93 |

TABLE 4-continued

Placement stability of the humanized monoclonal anti-PD-L1 antibody 5G11 injections at 25° C.

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| | Month 3 | 0.4 | 99.3 | 0.3 | 31.8 | 61.8 | 6.4 | 101 |
| | Month 6 | 0.5 | 99.1 | 0.4 | 43.4 | 46.8 | 9.8 | 95 |
| Example 9 | Day 0 | 0.1 | 99.8 | 0.1 | 46.5 | 50.7 | 2.8 | 93 |
| | Month 1 | 0.8 | 99.1 | 0.1 | 46.7 | 50.3 | 3 | 95 |
| | Month 2 | 1 | 98.8 | 0.2 | 48.5 | 48.7 | 2.8 | 88 |
| | Month 3 | 1.4 | 98.3 | 0.3 | 50 | 47.7 | 2.3 | 93 |
| | Month 6 | 1.8 | 97.8 | 0.4 | 52.5 | 44.3 | 3.2 | 95 |
| Example 10 | Day 0 | 0.2 | 99.8 | 0.0 | 28.6 | 60.2 | 9.2 | 90 |
| | Month 1 | 0.2 | 99.7 | 0.1 | 30.6 | 60.1 | 9.3 | 99 |
| | Month 2 | 0.2 | 99.6 | 0.2 | 32.1 | 59.2 | 8.8 | 92 |
| | Month 3 | 0.3 | 99.4 | 0.3 | 34.6 | 56.7 | 8.7 | 87 |
| | Month 6 | 0.4 | 99.2 | 0.4 | 41.2 | 49.7 | 9.2 | 83 |
| Example 11 | Day 0 | 0.1 | 99.8 | 0.1 | 30.3 | 63.4 | 6.3 | 103 |
| | Month 1 | 0.1 | 99.8 | 0.1 | 31.3 | 63.1 | 5.6 | 91 |
| | Month 2 | 0.2 | 99.8 | 0 | 32.4 | 63.3 | 4.3 | 93 |
| | Month 3 | 0.3 | 99.5 | 0.2 | 33.5 | 61.9 | 4.6 | 104 |
| | Month 6 | 0.4 | 99.3 | 0.3 | 36.6 | 56.4 | 7.0 | 95 |
| Example 12 | Day 0 | 0.1 | 99.9 | 0 | 30.2 | 63.6 | 6.2 | 96 |
| | Month 1 | 0.1 | 99.7 | 0.2 | 32.3 | 62.7 | 5 | 103 |
| | Month 2 | 0.2 | 99.8 | 0 | 33.4 | 61.4 | 5.2 | 106 |
| | Month 3 | 0.3 | 99.6 | 0.1 | 34.6 | 60.5 | 4.9 | 92 |
| | Month 6 | 0.4 | 99.4 | 0.2 | 37.1 | 56.6 | 6.3 | 95 |

The results show that after the samples of the formulation prescriptions of Examples 1 to 8 and Examples 10 to 12 of the present invention have been placed at 25° C. for 6 months, the content percentage of the aggregate, which is 0.3% to 0.9%, is increased by 0.4% to 0.6%; that of the degradation product increased by 0.0% to 0.5%, that of the main peak decreased by 0.2% to 0.9%; that of the acidic zone increased by 6.1% to 16.7%, while that of the basic zone changes less; and the binding activities of the antibodies are all higher than 80%. The results show that after the humanized monoclonal anti-PD-L1 antibody 5G11 injections of the present invention have been placed at 25° C. for 6 months, the content percentages for the aggregate and the degradation product change less, and the activities remain better.

EXAMPLE 16

Stability Study on the Humanized Monoclonal anti-PD-L1 Antibody 5G11 Injections at 40° C.

12 batches of the humanized monoclonal anti-PD-L1 antibody injection were prepared according to the methods of Examples 1-12. Each batch of the injections was placed in an environment at 40° C. and sampled for testing at Day 0, Week 2, and Week 4, respectively. Purity of the monoclonal antibody was determined by molecular sieve chromatography (SEC) and ion exchange chromatography (CEX), and the biological binding activity thereof by enzyme-linked immunosorbent assay (ELISA). Changes in the purities and activities of the humanized monoclonal anti-PD-L1 antibody injection during the placement at the high temperature of 40° C. was examined to evaluate the stability of the pharmaceutical composition of the present invention. The method for detecting the involved indicators is the same as in Example 13. The stability in the purities and the activities of the humanized monoclonal anti-PD-L1 antibody 5G11 injections at the high temperature of 40° C. is found in Table 5.

TABLE 5

Result of stability examination of the humanized monoclonal anti-PD-L1 antibody 5G11 injections at the high temperature of 40° C.

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| Example 1 | Day 0 | 0.2 | 99.7 | 0.0 | 28.4 | 61.4 | 10.2 | 102 |
| | Week 2 | 0.3 | 99.5 | 0.3 | 36.0 | 53.7 | 10.3 | 101 |
| | Week 4 | 0.3 | 99.2 | 0.5 | 42.1 | 47.8 | 10.2 | 98 |
| Example 2 | Day 0 | 0.2 | 99.8 | 0.1 | 30.5 | 63.1 | 6.4 | 100 |
| | Week 2 | 0.3 | 99.4 | 0.3 | 38.4 | 53.5 | 8.1 | 95 |
| | Week 4 | 0.4 | 98.9 | 0.6 | 45.6 | 45.2 | 9.2 | 100 |
| Example 3 | Day 0 | 0.2 | 99.8 | 0.0 | 28.5 | 62.2 | 9.3 | 100 |
| | Week 2 | 0.2 | 99.5 | 0.3 | 35.8 | 54.2 | 10.0 | 101 |
| | Week 4 | 0.3 | 99.1 | 0.6 | 46.8 | 43.0 | 10.2 | 88 |

TABLE 5-continued

Result of stability examination of the humanized monoclonal anti-PD-L1 antibody 5G11 injections at the high temperature of 40° C.

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| Example 4 | Day 0 | 0.3 | 99.7 | 0.0 | 28.4 | 61.5 | 10.1 | 93 |
| | Week 2 | 0.3 | 99.4 | 0.3 | 36.2 | 53.6 | 10.2 | 95 |
| | Week 4 | 0.4 | 99.2 | 0.4 | 42.7 | 47.3 | 10.0 | 95 |
| Example 5 | Day 0 | 0.3 | 99.7 | 0.0 | 28.1 | 61.5 | 10.4 | 93 |
| | Week 2 | 0.5 | 99.1 | 0.4 | 38.2 | 50.6 | 11.2 | 95 |
| | Week 4 | 0.9 | 98.2 | 0.9 | 46.7 | 40.3 | 13.0 | 95 |
| Example 6 | Day 0 | 0.2 | 99.8 | 0.1 | 30.4 | 63.4 | 6.2 | 99 |
| | Week 2 | 0.3 | 99.4 | 0.3 | 38.5 | 53.4 | 8.1 | 95 |
| | Week 4 | 0.4 | 98.9 | 0.6 | 45.6 | 45.2 | 9.2 | 98 |
| Example 7 | Day 0 | 0.2 | 99.7 | 0.0 | 27.3 | 67.4 | 5.3 | 103 |
| | Week 2 | 0.3 | 99.5 | 0.3 | 29.7 | 64.4 | 5.9 | 98 |
| | Week 4 | 0.3 | 99.2 | 0.5 | 42.7 | 49.4 | 7.8 | 95 |
| Example 8 | Day 0 | 0.3 | 99.6 | 0 | 26.9 | 65.9 | 7.2 | 81 |
| | Week 2 | 0.3 | 99.4 | 0.3 | 37.5 | 55.1 | 7.4 | NA |
| | Week 4 | 0.4 | 99.1 | 0.5 | 43.2 | 49.3 | 7.5 | 107 |
| Example 9 | Day 0 | 0.1 | 99.8 | 0.1 | 46.5 | 50.7 | 2.8 | 93 |
| | Week 2 | 0.8 | 80.1 | 0.4 | 75.4 | 21.0 | 3.6 | 29 |
| | Week 4 | 2.1 | 83.4 | 3.5 | 85.2 | 9.8 | 5.0 | 20 |
| Example 10 | Day 0 | 0.2 | 99.8 | 0.0 | 28.6 | 62.2 | 9.2 | 90 |
| | Week 2 | 0.2 | 99.5 | 0.3 | 36.5 | 53.0 | 10.5 | 86 |
| | Week 4 | 0.4 | 99.0 | 0.6 | 49.3 | 40.2 | 10.6 | 109 |
| Example 11 | Day 0 | 0.1 | 99.8 | 0.1 | 30.3 | 63.4 | 6.4 | 103 |
| | Week 2 | 0.4 | 99.0 | 0.6 | 37.9 | 50.0 | 12.0 | 95 |
| | Week 4 | 0.6 | 98.3 | 1.1 | 44.8 | 41.5 | 13.8 | 99 |
| Example 12 | Day 0 | 0.1 | 99.9 | 0.1 | 30.2 | 63.6 | 6.2 | 96 |
| | Week 2 | 0.2 | 99.3 | 0.4 | 36.6 | 54.4 | 9.0 | 111 |
| | Week 4 | 0.3 | 98.8 | 0.9 | 42.7 | 46.7 | 10.6 | 105 |

The results show that after the samples of the formulation prescriptions of Examples 1 to 8 and Examples 10 to 12 of the present invention have been placed at a high temperature of 40° C. for 4 weeks, the content percentage of the aggregate, which is 0.3% to 0.9%, is increased by 0.2% to 0.6%; that of the degradation product increased by 0.0% to 1.0%, that of the main peak decreased by 0.2% to 0.9%; and the binding activities of the antibodies all remain above 80%. The results show that in addition to the formulation prescription of Example 9, after the humanized monoclonal anti-PD-L1 antibody 5G11 injections of the present invention have been placed at the high temperature of 40° C. for 4 weeks, the content percentages for the aggregate and the degradation product change less, the activities thereof all remains better.

EXAMPLE 17

Shaking Stability Study on the Humanized Monoclonal anti-PD-L1 Antibody 5G11 Injections Each batch of the injections was placed in an environment at a constant temperature of 25° C. while shaking, and sampled for testing at Week 0, Week 1, and Week 2. Purity was determined by molecular sieve chromatography (SEC) and ion exchange chromatography (CEX), to examine the change in the purities of the humanized monoclonal anti-PD-L1 antibody 5G11 injections during the shaking at 25° C., and biological binding activity was determined by enzyme-linked immunosorbent assay (ELISA), to evaluate the stability of the pharmaceutical composition of the present invention. The method for detecting the involved indicators is the same as in Example 13. The stability in the purities and the activities of the humanized monoclonal anti-PD-L1 antibody 5G11 injections in shaking at 25° C. is found in Table 6.

TABLE 6

Result of shaking stability examination of the humanized monoclonal anti-PD-L1 antibody 5G11 injections at 25° C.

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| Example 1 | Day 0 | 0.1 | 99.9 | 0.0 | 30.5 | 63.3 | 6.2 | 102 |
| | Week 1 | 0.1 | 99.8 | 0.0 | 30.6 | 62.8 | 6.7 | 86 |
| | Week 2 | 0.1 | 99.8 | 0.0 | 30.7 | 62.5 | 6.8 | 90 |

TABLE 6-continued

Result of shaking stability examination of the humanized monoclonal anti-PD-L1 antibody 5G11 injections at 25° C.

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| Example 2 | Day 0 | 0.1 | 99.9 | 0.0 | 30.6 | 63.1 | 6.2 | 96 |
| | Week 1 | 0.1 | 99.8 | 0.1 | 31.6 | 62.1 | 6.3 | 94 |
| | Week 2 | 0.2 | 99.8 | 0.1 | 31.7 | 61.7 | 6.6 | 98 |
| Example 3 | Day 0 | 0.2 | 99.8 | 0.0 | 28.2 | 62.0 | 9.8 | 100 |
| | Week 1 | 0.2 | 99.7 | 0.0 | 29.1 | 61.4 | 9.5 | 88 |
| | Week 2 | 0.2 | 99.7 | 0.1 | 29.1 | 61.4 | 9.5 | 98 |
| Example 4 | Day 0 | 0.3 | 99.7 | 0.0 | 28.4 | 61.5 | 10.1 | 93 |
| | Week 1 | 0.4 | 99.6 | 0.1 | 29.5 | 61.2 | 9.3 | 88 |
| | Week 2 | 0.4 | 99.6 | 0.1 | 29.6 | 61.2 | 9.2 | 94 |
| Example 5 | Day 0 | 0.3 | 99.7 | 0.0 | 30.5 | 63.3 | 6.2 | 105 |
| | Week 1 | 0.3 | 99.7 | 0.0 | 31.2 | 62.1 | 6.7 | 98 |
| | Week 2 | 0.4 | 99.6 | 0.0 | 31.7 | 61.5 | 6.9 | 94 |
| Example 6 | Day 0 | 0.1 | 99.9 | 0.0 | 30.4 | 63.4 | 6.2 | 91 |
| | Week 1 | 0.1 | 99.8 | 0.0 | 31.1 | 63.0 | 5.9 | 101 |
| | Week 2 | 0.2 | 99.8 | 0.0 | 31.6 | 62.2 | 6.2 | 94 |
| Example 7 | Day 0 | 0.2 | 99.7 | 0.0 | 27.3 | 67.4 | 5.3 | 103 |
| | Week 1 | 0.3 | 99.7 | 0.0 | 27.0 | 67.1 | 5.7 | 95 |
| | Week 2 | 0.3 | 99.7 | 0.1 | 29.7 | 64.4 | 5.9 | 87 |
| Example 8 | Day 0 | 0.3 | 99.6 | 0 | 26.9 | 65.9 | 7.2 | 81 |
| | Week 1 | 0.3 | 99.6 | 0 | 26.6 | 65.6 | 7.8 | 93 |
| | Week 2 | 0.3 | 99.6 | 0.1 | 28.1 | 66.1 | 5.8 | 88 |
| Example 9 | Day 0 | 0.1 | 99.8 | 0.1 | 46.5 | 50.7 | 2.8 | 93 |
| | Week 1 | 0.8 | 98.7 | 0.3 | 50.1 | 47.0 | 2.9 | 84 |
| | Week 2 | 1.0 | 98.8 | 0.2 | 50.7 | 46.4 | 2.9 | 86 |
| Example 10 | Day 0 | 0.2 | 99.8 | 0.0 | 28.6 | 62.2 | 9.2 | 90 |
| | Week 1 | 0.2 | 99.7 | 0.1 | 28.8 | 61.7 | 9.5 | 92 |
| | Week 2 | 0.2 | 99.7 | 0.1 | 29.1 | 61.5 | 9.4 | 103 |
| Example 11 | Day 0 | 0.1 | 99.8 | 0.1 | 30.3 | 63.4 | 6.4 | 103 |
| | Week 1 | 0.1 | 99.8 | 0.1 | 31.7 | 60.9 | 7.5 | 99 |
| | Week 2 | 0.1 | 99.7 | 0.1 | 31.7 | 61.1 | 7.2 | 87 |
| Example 12 | Day 0 | 0.1 | 99.9 | 0.1 | 30.2 | 63.6 | 6.2 | 96 |
| | Week 1 | 0.1 | 99.7 | 0.1 | 31.8 | 61.4 | 6.8 | 109 |
| | Week 2 | 0.2 | 99.7 | 0.1 | 32.2 | 61.9 | 5.9 | 103 |

The results show that after the samples of the prescriptions of Examples 1 to 8 and Examples 10 to 12 of the present invention have been in shaking in an environment at a constant temperature of 25° C. for 2 weeks, the content percentage of the aggregate, which is 0.1% to 0.4%, is increased by 0.0% to 0.1%; that of the degradation product increased by 0.0% to 0.1%; that of the main peak decreased by 0.1% to 0.2%; that of the acidic zone increased by 0.2% to 2.4%, while that of the basic zone has no significant change; and the binding activities of the antibodies remained above 80%. The results show that after the humanized monoclonal anti-PD-L1 antibody 5G11 injections of the present invention have been in shaking at 25° C. for 2 weeks, the individual indicators all change less, while the individual purities and the activities remains stable, indicating good shaking stability. Example 18 Freeze-thaw stability study on the humanized monoclonal anti-PD-L1 antibody 5G11 injections Each batch of the injections was freeze-stored at −20° C. for 2 days, thawed in an environment at a constant temperature of 25° C. for 2 days, and sampled for testing, for 3 cycles. Purity was determined by molecular sieve chromatography (SEC) and ion exchange chromatography (CEX), and the biological binding activity by enzyme-linked immunosorbent assay (ELISA). Change in the purities and the activities of the humanized monoclonal anti-PD-L1 antibody 5G11 injections during freeze and thaw was examined to evaluate the stability of the pharmaceutical composition of the present invention. The method for detecting the involved indicators is the same as in Example 13. The stability in the purities and activities after freeze-thaw is found in Table 7.

TABLE 7

Freeze-thaw stability of the humanized monoclonal anti-PD-L1 antibody 5G11 injections

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| Example 1 | Day 0 | 0.1 | 99.9 | 0 | 30.5 | 63.3 | 6.2 | 92 |
| | Freeze-thawed 1 time | 0.1 | 99.9 | 0 | 30.5 | 63.3 | 6.2 | 96 |

TABLE 7-continued

Freeze-thaw stability of the humanized monoclonal anti-PD-L1 antibody 5G11 injections

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| | Freeze-thawed 2 times | 0.1 | 99.8 | 0 | 30.5 | 63.2 | 6.3 | 98 |
| | Freeze-thawed 3 times | 0.1 | 99.8 | 0 | 30.7 | 63 | 6.4 | 84 |
| Example 2 | Day 0 | 0.1 | 99.9 | 0 | 30.6 | 63.1 | 6.2 | 96 |
| | Freeze-thawed 1 time | 0.1 | 99.9 | 0 | 30.6 | 63.1 | 6.2 | 101 |
| | Freeze-thawed 2 times | 0.1 | 99.8 | 0.1 | 30.6 | 63.1 | 6.3 | 96 |
| | Freeze-thawed 3 times | 0.1 | 99.8 | 0.1 | 31.1 | 62.6 | 6.3 | 87 |
| Example 3 | Day 0 | 0.1 | 99.9 | 0 | 30.9 | 63.1 | 6 | 101 |
| | Freeze-thawed 1 time | 0.2 | 99.8 | 0 | 30.9 | 63.1 | 6 | 102 |
| | Freeze-thawed 2 times | 0.2 | 99.8 | 0.1 | 31.2 | 62.9 | 6 | 105 |
| | Freeze-thawed 3 times | 0.2 | 99.7 | 0.1 | 31.2 | 62.7 | 6.1 | 95 |
| Example 4 | Day 0 | 0.1 | 99.9 | 0 | 30.6 | 63.2 | 6.2 | 93 |
| | Freeze-thawed 1 time | 0.1 | 99.9 | 0 | 30.6 | 63.2 | 6.2 | 92 |
| | Freeze-thawed 2 times | 0.1 | 99.8 | 0 | 30.8 | 62.9 | 6.3 | 86 |
| | Freeze-thawed 3 times | 0.2 | 99.8 | 0 | 31.2 | 62.5 | 6.3 | 94 |
| Example 5 | Day 0 | 0.3 | 99.7 | 0 | 30.5 | 63.3 | 6.2 | 95 |
| | Freeze-thawed 1 time | 0.3 | 99.7 | 0 | 30.5 | 63.3 | 6.2 | 104 |
| | Freeze-thawed 2 times | 0.3 | 99.7 | 0 | 30.7 | 63 | 6.3 | 84 |
| | Freeze-thawed 3 times | 0.4 | 99.6 | 0 | 30.8 | 62.9 | 6.3 | 101 |
| Example 6 | Day 0 | 0.1 | 99.9 | 0 | 30.4 | 63.4 | 6.2 | 89 |
| | Freeze-thawed 1 time | 0.1 | 99.9 | 0 | 30.4 | 63.4 | 6.2 | 91 |
| | Freeze-thawed 2 times | 0.1 | 99.8 | 0 | 30.7 | 63.3 | 6 | 103 |
| | Freeze-thawed 3 times | 0.2 | 99.8 | 0.1 | 31 | 62.7 | 6.3 | 104 |
| Example 7 | Day 0 | 0.2 | 99.7 | 0 | 27.3 | 67.4 | 5.3 | 103 |
| | Freeze-thawed 1 time | 0.1 | 99.9 | 0 | 27 | 67.1 | 5.7 | 101 |
| | Freeze-thawed 2 times | 0.1 | 99.8 | 0.1 | 27.1 | 67 | 5.9 | 99 |
| | Freeze-thawed 3 times | 0.2 | 99.8 | 0 | 27.3 | 67.2 | 5.5 | 104 |
| Example 8 | Day 0 | 0.3 | 99.6 | 0 | 26.9 | 65.9 | 7.2 | 81 |
| | Freeze-thawed 1 time | 0.3 | 99.6 | 0.1 | 27 | 65.6 | 7.4 | 106 |
| | Freeze-thawed 2 times | 0.4 | 99.5 | 0.1 | 27.1 | 66 | 6.9 | 88 |
| | Freeze-thawed 3 times | 0.4 | 99.5 | 0.1 | 27.2 | 66.2 | 6.6 | 87 |
| Example 9 | Day 0 | 0.1 | 99.8 | 0.1 | 46.5 | 50.7 | 2.8 | 93 |
| | Freeze-thawed 1 time | 0.1 | 99.8 | 0.1 | 46.3 | 50.2 | 3.5 | 91 |
| | Freeze-thawed 2 times | 0.2 | 99.6 | 0.2 | 46.9 | 50 | 3.1 | 88 |
| | Freeze-thawed 3 times | 0.2 | 99.5 | 0.3 | 47 | 49.9 | 3.1 | 101 |
| Example 10 | Day 0 | 0.2 | 99.8 | 0 | 28.6 | 62.2 | 9.2 | 90 |
| | Freeze-thawed 1 time | 0.2 | 99.8 | 0 | 28.7 | 61.1 | 10.2 | 104 |
| | Freeze-thawed 2 times | 0.2 | 99.7 | 0.1 | 29 | 61 | 10 | 95 |
| | Freeze-thawed 3 times | 0.2 | 99.7 | 0.1 | 29.1 | 60.5 | 10.4 | 88 |
| Example 11 | Day 0 | 0.1 | 99.8 | 0.1 | 30.3 | 63.4 | 6.4 | 103 |
| | Freeze-thawed 1 time | 0.1 | 99.8 | 0.1 | 30.1 | 63 | 6.9 | 87 |
| | Freeze-thawed 2 times | 0.1 | 99.7 | 0.2 | 29.9 | 62.8 | 7.3 | 85 |

TABLE 7-continued

Freeze-thaw stability of the humanized monoclonal anti-PD-L1 antibody 5G11 injections

| Example No. | Examination time | SEC Purity (%) | | | CEX Purity (%) | | | Activity (%) |
|---|---|---|---|---|---|---|---|---|
| | | Aggregate | Main peak | Degradation product | Acidic zone | Main peak | Basic zone | |
| | Freeze-thawed 3 times | 0.1 | 99.7 | 0.2 | 29.8 | 62.5 | 7.7 | 89 |
| Example 12 | Day 0 | 0.1 | 99.9 | 0.1 | 30.2 | 63.6 | 6.2 | 96 |
| | Freeze-thawed 1 time | 0.1 | 99.8 | 0.1 | 30.1 | 63.4 | 6.5 | 85 |
| | Freeze-thawed 2 times | 0.1 | 99.8 | 0.1 | 29.8 | 63 | 7.2 | 94 |
| | Freeze-thawed 3 times | 0.2 | 99.7 | 0.1 | 29.7 | 62.9 | 7.4 | 93 |

The results show that after the prescriptions of Examples 1 to 12 have been freeze-thawed 3 times, the content percentage of the aggregate, which is 0.2% to 0.4%, is increased only by 0% to 0.1%; that of the degradation product increased only by 0% to 0.2%; that of the main peak decreased only by 0% to 0.3%; those of the acidic and basic zones have no significant change; and the binding activities of the antibodies remained above 80%. The results show that after the samples of the prescriptions of Examples 1 to 12 have been freeze-thawed 3 times, the individual indicators change within a small range, indicating good freeze-thaw stability.

According to the disclosure of the present invention, although the compositions and methods of the present invention have been described according to the preferred embodiments, it will be apparent to those skilled in the art that changes can be made to the compositions and/or methods described herein and the steps or the sequence of steps, without departing from the concept, spirit, and scope of the present invention.

The disclosures of all documents cited herein are hereby incorporated by reference to the extent that they would provide exemplary, procedural, and other details supplementary to the content described herein.

The invention claimed is:

1. A pharmaceutical composition of humanized monoclonal anti-PD-L1 antibody, comprising:
   (a) the humanized monoclonal anti-PD-L1 antibody at a mass concentration of 10 mg/mL,
   (b) sucrose at a mass concentration of 80 mg/mL,
   (c) polysorbate-80 at a mass concentration of 0.2 mg/ml,
   (d) histidine at a molar concentration of 10 mM, and
   (e) hydrochloric acid in an appropriate amount, for adjusting the pH of the composition to 5.5, wherein the humanized monoclonal anti-PD-L1 antibody comprises heavy chains CDR1, CDR2, and CDR3 having the amino acid sequences shown in SEQ ID NO: 1, SEQ ID NO: 2, and SEQ ID NO: 3, respectively, and light chains CDR1, CDR2, and CDR3 having the amino acid sequences shown in SEQ ID NO: 7, SEQ ID NO: 8, and SEQ ID NO: 9, respectively.

2. A pharmaceutical composition of humanized monoclonal anti-PD-L1 antibody, comprising:
   (a) the humanized monoclonal anti-PD-L1 antibody at a mass concentration of 30 mg/mL,
   (b) sucrose at a mass concentration of 80 mg/mL,
   (c) polysorbate-80 at a mass concentration of 0.2 mg/ml,
   (d) histidine at a molar concentration of 10 mM, and
   (e) hydrochloric acid in an appropriate amount, for adjusting the pH of the composition to 5.5, wherein the humanized monoclonal anti-PD-L1 antibody comprises heavy chains CDR1, CDR2, and CDR3 having the amino acid sequences shown in SEQ ID NO: 1, SEQ ID NO: 2, and SEQ ID NO: 3, respectively, and light chains CDR1, CDR2, and CDR3 having the amino acid sequences shown in SEQ ID NO: 7, SEQ ID NO: 8, and SEQ ID NO: 9, respectively.

3. The pharmaceutical composition of claim 2, wherein the humanized monoclonal anti-PD-L1 antibody comprises the amino acid sequence as follows:
   a heavy chain variable region as shown in SEQ ID NO: 13; a light chain variable region as shown in SEQ ID NO: 15.

4. The pharmaceutical composition of claim 2, wherein the humanized monoclonal anti-PD-L1 antibody comprises the heavy chain amino acid sequence as shown in SEQ ID NO: 17, and the light chain amino acid sequence as shown in SEQ ID NO: 18.

5. The pharmaceutical composition of claim 1, wherein the humanized monoclonal anti-PD-L1 antibody comprises the amino acid sequence as follows: a heavy chain variable region as shown in SEQ ID NO: 13; a light chain variable region as shown in SEQ ID NO: 15.

6. The pharmaceutical composition of claim 1, wherein the humanized monoclonal anti-PD-L1 antibody comprises the heavy chain amino acid sequence as shown in SEQ ID NO: 17, and the light chain amino acid sequence as shown in SEQ ID NO: 18.

* * * * *

SEQUENCE LISTING

```
<160> NUMBER OF SEQ ID NOS: 21

<210> SEQ ID NO 1
<211> LENGTH: 5
<212> TYPE: PRT
<213> ORGANISM: Mus sp.

<400> SEQUENCE: 1

Thr Tyr Gly Val His
1               5

<210> SEQ ID NO 2
<211> LENGTH: 16
<212> TYPE: PRT
<213> ORGANISM: Mus sp.

<400> SEQUENCE: 2

Val Ile Trp Arg Gly Val Thr Thr Asp Tyr Asn Ala Ala Phe Met Ser
1               5                   10                  15

<210> SEQ ID NO 3
<211> LENGTH: 8
<212> TYPE: PRT
<213> ORGANISM: Mus sp.

<400> SEQUENCE: 3

Leu Gly Phe Tyr Ala Met Asp Tyr
1               5

<210> SEQ ID NO 4
<211> LENGTH: 5
<212> TYPE: PRT
<213> ORGANISM: Mus sp.

<400> SEQUENCE: 4
```

```
Ser Tyr Gly Met Ser
1               5

<210> SEQ ID NO 5
<211> LENGTH: 16
<212> TYPE: PRT
<213> ORGANISM: Mus sp.

<400> SEQUENCE: 5

Ser Ile Ser Ser Gly Gly Ser Thr Tyr Tyr Pro Asp Ser Val Lys Gly
1               5                   10                  15

<210> SEQ ID NO 6
<211> LENGTH: 8
<212> TYPE: PRT
<213> ORGANISM: Mus sp.

<400> SEQUENCE: 6

Gly Tyr Asp Ser Gly Phe Ala Tyr
1               5

<210> SEQ ID NO 7
<211> LENGTH: 11
<212> TYPE: PRT
<213> ORGANISM: Mus sp.

<400> SEQUENCE: 7

Lys Ala Ser Gln Ser Val Ser Asn Asp Val Ala
1               5                   10

<210> SEQ ID NO 8
<211> LENGTH: 7
<212> TYPE: PRT
<213> ORGANISM: Mus sp.

<400> SEQUENCE: 8

Tyr Ala Ala Asn Arg Tyr Thr
1               5

<210> SEQ ID NO 9
<211> LENGTH: 9
<212> TYPE: PRT
<213> ORGANISM: Mus sp.

<400> SEQUENCE: 9

Gln Gln Asp Tyr Thr Ser Pro Tyr Thr
1               5

<210> SEQ ID NO 10
<211> LENGTH: 14
<212> TYPE: PRT
<213> ORGANISM: Mus sp.

<400> SEQUENCE: 10

Ala Ser Gln Ser Val Ser Thr Ser Ser Ser Phe Met His
1               5                   10

<210> SEQ ID NO 11
<211> LENGTH: 7
<212> TYPE: PRT
<213> ORGANISM: Mus sp.

<400> SEQUENCE: 11

Tyr Ala Ser Asn Leu Glu Ser
```

```
1               5

<210> SEQ ID NO 12
<211> LENGTH: 9
<212> TYPE: PRT
<213> ORGANISM: Mus sp.

<400> SEQUENCE: 12

Gln His Ser Trp Glu Ile Pro Tyr Thr
1               5

<210> SEQ ID NO 13
<211> LENGTH: 116
<212> TYPE: PRT
<213> ORGANISM: Artificial sequence
<220> FEATURE:
<223> OTHER INFORMATION: synthesized

<400> SEQUENCE: 13

Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
            20                  25                  30

Gly Val His Trp Ile Arg Gln Pro Pro Gly Lys Ala Leu Glu Trp Leu
        35                  40                  45

Gly Val Ile Trp Arg Gly Val Thr Thr Asp Tyr Asn Ala Ala Phe Met
    50                  55                  60

Ser Arg Leu Thr Ile Thr Lys Asp Asn Ser Lys Asn Gln Val Val Leu
65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser
        115

<210> SEQ ID NO 14
<211> LENGTH: 116
<212> TYPE: PRT
<213> ORGANISM: Artificial sequence
<220> FEATURE:
<223> OTHER INFORMATION: synthesized

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Arg Ser Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Ser
```

```
               115

<210> SEQ ID NO 15
<211> LENGTH: 107
<212> TYPE: PRT
<213> ORGANISM: Artificial sequence
<220> FEATURE:
<223> OTHER INFORMATION: synthesized

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ala Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Thr Ser Pro Tyr
                85                  90                  95

Thr Phe Gly Gln Gly Thr Lys Leu Glu Ile Lys
            100                 105

<210> SEQ ID NO 16
<211> LENGTH: 111
<212> TYPE: PRT
<213> ORGANISM: Artificial sequence
<220> FEATURE:
<223> OTHER INFORMATION: synthesized

<400> SEQUENCE: 16

Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Ser Thr Ser
            20                  25                  30

Ser Ser Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Trp
                85                  90                  95

Glu Ile Pro Tyr Thr Phe Gly Gln Gly Thr Lys Leu Glu Ile Lys
            100                 105                 110

<210> SEQ ID NO 17
<211> LENGTH: 446
<212> TYPE: PRT
<213> ORGANISM: Artificial sequence
<220> FEATURE:
<223> OTHER INFORMATION: synthesized

<400> SEQUENCE: 17

Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
            20                  25                  30
```

```
Gly Val His Trp Ile Arg Gln Pro Gly Lys Ala Leu Glu Trp Leu
         35                  40                  45

Gly Val Ile Trp Arg Gly Val Thr Thr Asp Tyr Asn Ala Ala Phe Met
 50                  55                  60

Ser Arg Leu Thr Ile Thr Lys Asp Asn Ser Lys Asn Gln Val Val Leu
 65                  70                  75                  80

Thr Met Asn Asn Met Asp Pro Val Asp Thr Ala Thr Tyr Tyr Cys Ala
                 85                  90                  95

Arg Leu Gly Phe Tyr Ala Met Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
                260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

```
<210> SEQ ID NO 18
<211> LENGTH: 214
<212> TYPE: PRT
<213> ORGANISM: Artificial sequence
<220> FEATURE:
<223> OTHER INFORMATION: synthesized

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ala Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Thr Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 446
<212> TYPE: PRT
<213> ORGANISM: Artificial sequence
<220> FEATURE:
<223> OTHER INFORMATION: synthesized

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Arg Ser Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Asp Cys Ala
                85                  90                  95
```

Arg Gly Tyr Asp Ser Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 20
<211> LENGTH: 218
<212> TYPE: PRT
<213> ORGANISM: Artificial sequence
<220> FEATURE:
<223> OTHER INFORMATION: synthesized

<400> SEQUENCE: 20

Asp Ile Val Leu Thr Gln Ser Pro Ala Ser Leu Ala Val Ser Pro Gly
1               5                   10                  15

```
Gln Arg Ala Thr Ile Thr Cys Arg Ala Ser Gln Ser Val Ser Thr Ser
                20                  25                  30

Ser Ser Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln His Ser Trp
                85                  90                  95

Glu Ile Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 21
<211> LENGTH: 442
<212> TYPE: PRT
<213> ORGANISM: Artificial sequence
<220> FEATURE:
<223> OTHER INFORMATION: synthesized

<400> SEQUENCE: 21

Gln Ile Thr Leu Lys Glu Ser Gly Pro Thr Leu Val Lys Pro Thr Gln
 1               5                  10                  15

Thr Leu Thr Leu Thr Cys Thr Val Ser Gly Phe Ser Leu Ser Thr Tyr
                20                  25                  30

Gly Val His Trp Ile Arg Gln Pro Pro Gly Lys Ala Leu Glu Trp Leu
        35                  40                  45

Gly Val Ile Trp Arg Gly Val Thr Thr Asp Tyr Asn Ala Ala Phe Met
 50                  55                  60

Ser Arg Leu Thr Ile Thr Lys Asp Asn Ser Lys Asn Gln Val Val Leu
 65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
            210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly
            435                 440
```